(12) United States Patent
Seippel et al.

(10) Patent No.: US 7,767,440 B2
(45) Date of Patent: Aug. 3, 2010

(54) COVER FOR A HYBRIDIZATION CHAMBER

(75) Inventors: Martin Seippel, Brussels (DE);
Sandrine Hamels, Malonne (BE);
Christopher VanHuffel, Brussels (BE)

(73) Assignee: Eppendorf AG, Hamburg (DE)

( * ) Notice: Subject to any disclaimer, the term of this patent is extended or adjusted under 35 U.S.C. 154(b) by 1359 days.

(21) Appl. No.: 10/931,521

(22) Filed: Sep. 1, 2004

(65) Prior Publication Data
US 2005/0118708 A1 Jun. 2, 2005

(30) Foreign Application Priority Data
Sep. 3, 2003 (DE) ................ 103 40 473

(51) Int. Cl.
*C12M 1/34* (2006.01)
(52) U.S. Cl. .............. 435/287.2; 435/287.9; 435/288.3; 435/293.1; 359/398; 422/102
(58) Field of Classification Search ............... 359/398; 435/287.9, 288.3, 293.1
See application file for complete search history.

(56) References Cited

U.S. PATENT DOCUMENTS

| 4,299,920 | A | * | 11/1981 | Peters | 435/288.4 |
| 5,496,697 | A | * | 3/1996 | Parce et al. | 435/5 |
| 5,571,721 | A | * | 11/1996 | Turner | 435/305.1 |
| 6,258,593 | B1 | | 7/2001 | Schembri et al. | 435/287.2 |
| 2003/0235518 | A1 | | 12/2003 | Shea et al. | 422/102 |

FOREIGN PATENT DOCUMENTS

| DE | 100 02 920 | | 7/2001 |
| DE | 100 04 801 | | 8/2001 |
| WO | WO 02/072264 A1 | * | 9/2002 |

* cited by examiner

*Primary Examiner*—William H Beisner
(74) *Attorney, Agent, or Firm*—Vidas, Arrett & Steinkraus PA

(57) ABSTRACT

Cover of a hybridization chamber with a peripheral frame with filling and ventilation holes extending from the upper face to the lower face of the frame, a peripheral shoulder outside the filling and ventilation holes on the lower face of the frame, a cover wall arranged within the frame, flush with its lower face and downwardly offset relative to its upper face and which substantially consists of at least one resilient plastics material.

19 Claims, 3 Drawing Sheets

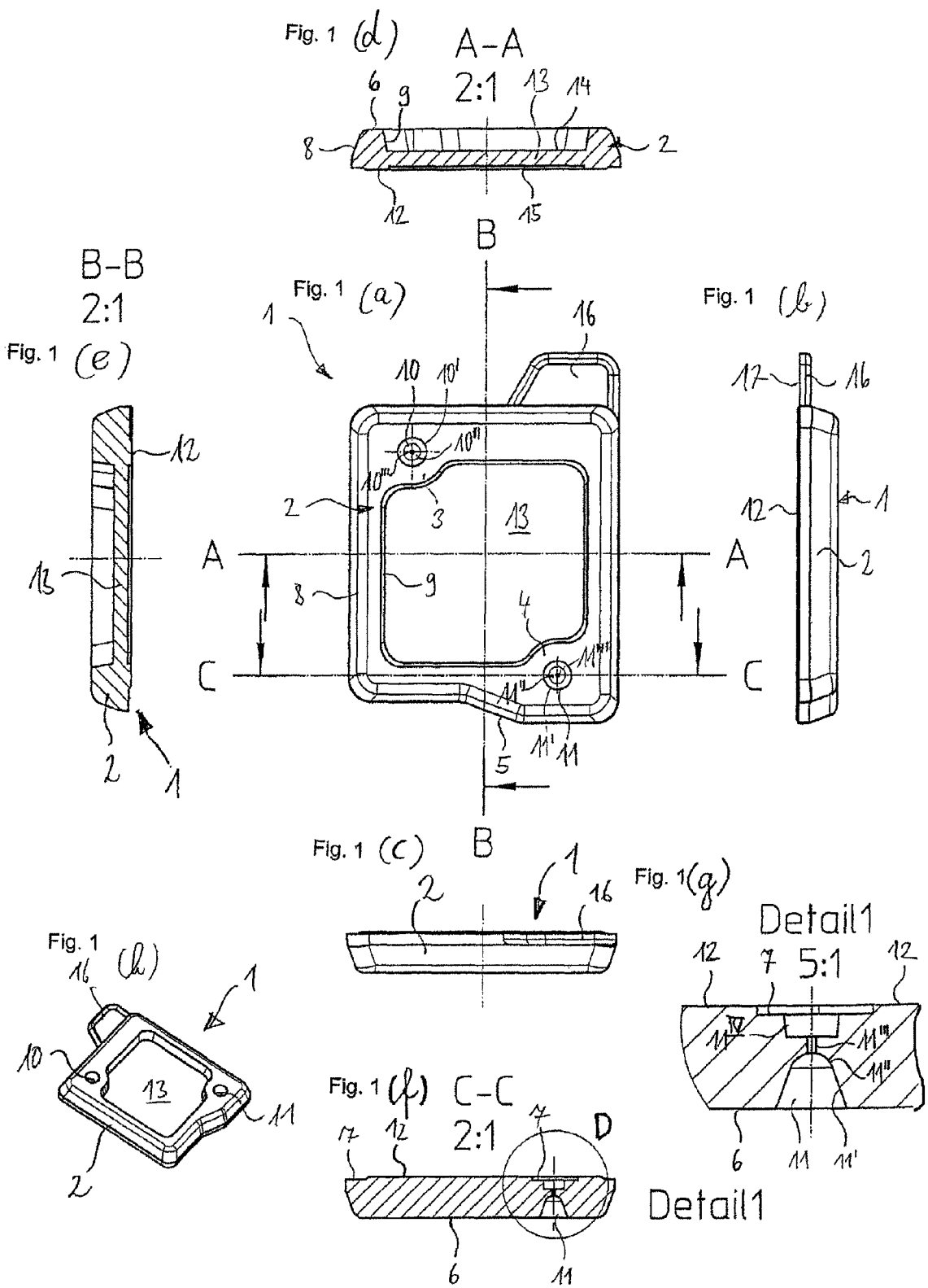

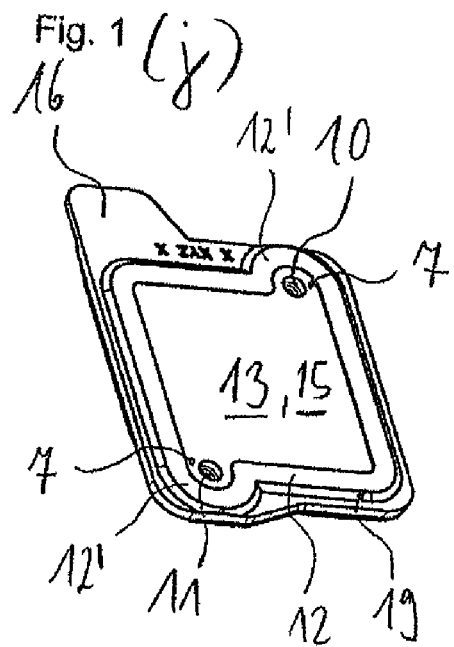
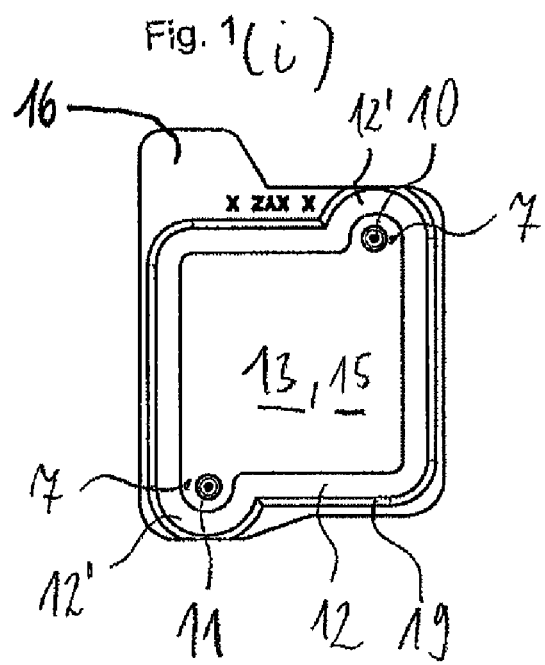

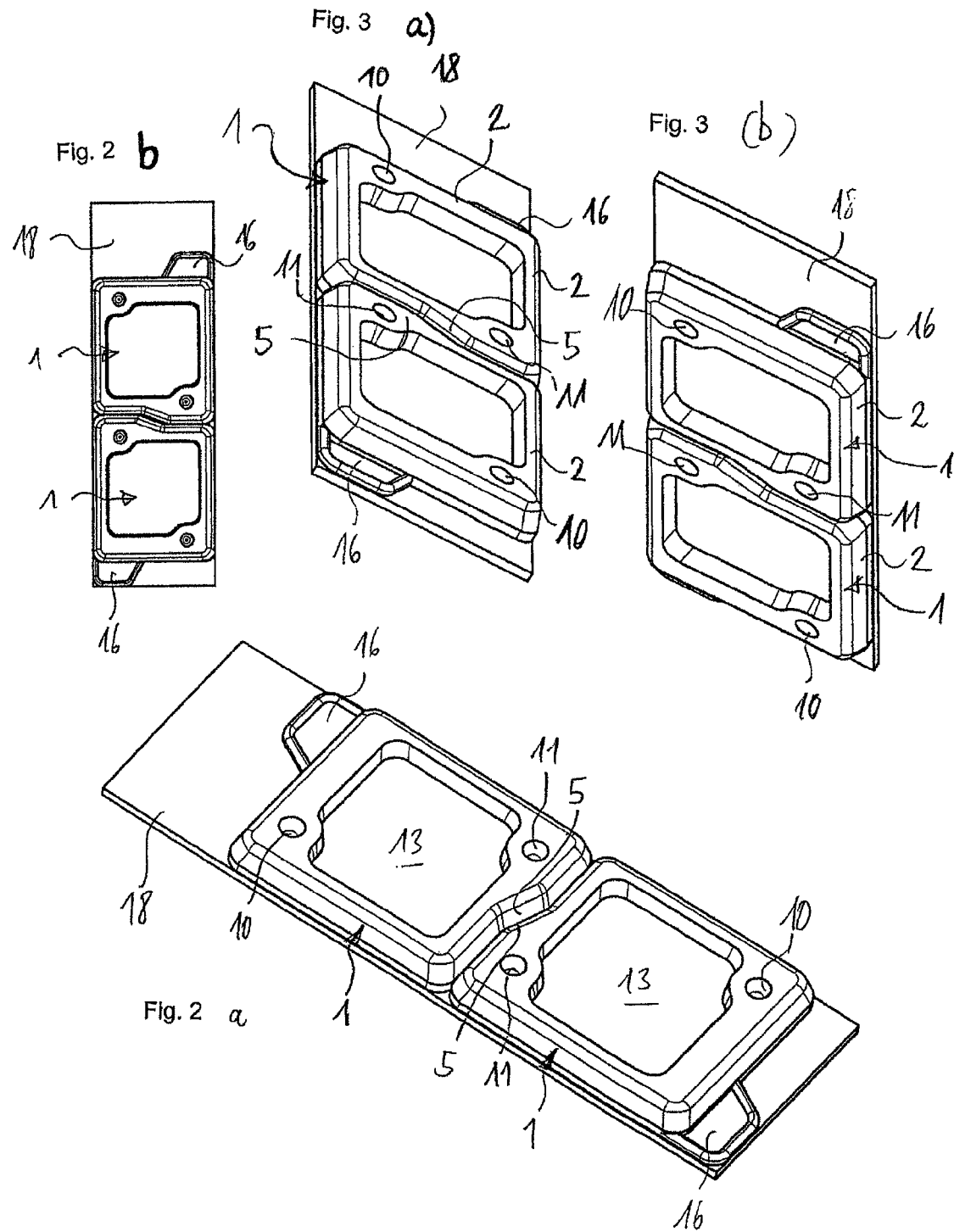

COVER FOR A HYBRIDIZATION CHAMBER

The invention relates to a cover for a hybridization chamber.

Nucleic acid hybridization makes it possible to establish the existence or position of a specific nucleic acid sequence in a mixture solution of molecules or a histological section. It has many different possibilities for use in research, for example gene expression analysis or the determination of point mutation (SNP Single Nucleotide Polymorphism). Moreover it is used in the diagnosis of inherited diseases or a susceptibility for this, personal identification or research into genealogical relationships.

In hybridization, use is made of the phenomenon that two mutually complementary nucleic acid single strands in solution form a double strand when they come together under specific buffer and temperature conditions. This double strand formation is called hybridization.

For hybridization, single stranded nucleic acid fragments are immobilised on a solid phase. Generally the base sequence (sequence) of the immobilised nucleic acid is known. According to agreement [Phimister, Nature Genetics 21, 1-1 (1999)] the immobilised nucleic acid is referred to as the English 'probe'.

The nucleic acid to be examined is referred to according to the same terminology as the English 'target' (target nucleic acid). As a rule it is marked with a label which allows detection. Generally fluorescent dyes or radioisotopes are used as labels. However labels, such as for example metals (gold, silver, platinum) or enzymes are also used.

With microchip technology unmarked nucleic acids are fixed onto a support in the form of point-shaped regions (spots). As a rule the support is a microscope slide (slide) as is known from microscopy. Other materials are also used as the fixed phase, preferably highly transparent plastics or silicon chips.

The diameter of the spots generally lies in the region of at least μm to hundreds of μm. The thickness of the spots varies from a few spots per slide up to several hundred thousand parts per cm$^2$. Furthermore the spots are arranged in a precisely determined pattern (microarray). Then a solution with the target molecules is applied onto the microarray. With the addition of heat, the hybridization takes place over a period of a few minutes up to many hours. Then the hybridization solution is removed and the support washed. Subsequently, by quantative detection of the label it is established whether a binding of the marked nucleic acids has taken place at specific target fields on the microchip.

Instead of microarrays arranged in spots, histological sections are also examined by 'in situ' hybridization on such supports. To this end, tissue sections are transferred to a slide and the nucleic acids contained therein converted into single stranded form by fixation. The hybridization takes place in a similar manner to that described above for microarrays.

A further possible use of the hybridization chamber proposed here is the incubation of protein microarrays and tissue sections with antibody solutions and other specific binding molecules.

To carry out the hybridization it is known to provide the microarray on the support with a cover, into which solution with the DNA or RNA probes is filled.

A known cover consists of a polycarbonate film with a wall thickness of approximately 0.2 mm and a hood-shaped raised part to construct the hybridization chamber. The edge region of the film surrounding the raised part is bonded to the support by means of dual-action adhesive tapes. The hybridization chamber formed between the raised part and the support can be filled and optionally emptied via filling and ventilation holes on the upper surface. The cover containing the fluid is removed from the support many times.

A disadvantage with known covers is that by attaching a pipette tip via the small holes in the thin walled film, filling and optionally emptying is difficult. Bubbles are easily introduced when filling. Spots covered by bubbles are excluded from the hybridization. Moreover during the course of the hybridization leaks can easily occur between the cover and the support. This is particularly when the chamber is shaken to intensify the hybridization and shorten the hybridization time. As a result it can lead to fluid loss and the introduction of air with disadvantageous effects on the hybridization. Releasing the rigid cover before rinsing the support is also problematical. During this the support can break as a result of bending forces.

Taking this as a basis, the object of the invention is to provide a cover of a hybridization chamber which has improved features for use.

The object is achieved by a cover with the features of claim 1. Advantageous embodiments of the cover are disclosed in the sub claims.

The cover of a hybridization chamber according to the invention has
- a peripheral frame with filling and ventilation holes extending from the upper face to the lower face of the frame,
- a peripheral shoulder outside the filling and ventilation holes on the lower face of the frame,
- a cover wall arranged inside the frame substantially flush with its lower face and downwardly offset relative to its upper face and
- substantially consists of at least one resilient plastics material.

The cover according to the invention can be connected by bonding the peripheral shoulder protruding from the lower face of the frame to the upper face of a support for a microarray or tissue sections. For example an adhesive is directly applied thereto or an adhesive tape used. When the frame is stuck on, the upper face can advantageously be used for the application of a compressing tool. For example the frame can be pressed on by rolling a cylindrical tool. The compression forces are directly introduced into the bond located thereunder.

A hybridization chamber is produced by joining the cover to the support. This can be filled with fluid through a filling hole, for example by attaching a pipette tip. The frame has a greater height than the cover wall. Therefore it is possible to form a relatively deep (for example funnel-shaped) filling hole into which a pipette tip can be sealingly inserted. Thus the introduction of air can be advantageously avoided during filling. The substantially flush sealing of the cover wall to the lower face facilitates steady and bubble-free filling with fluid of the cavity between the cover wall, shoulder and support. During filling, the air escapes out of the interior of the hybridization chamber through a ventilation hole.

The downwardly displaced cover wall has a greater flexibility than the frame. Possible loss of fluid, for example by evaporation or leakage can be compensated for by the bulging out of the cover wall toward the support. Introduction of air is thereby avoided. Optionally a pipette tip can be sealingly placed on a ventilation hole to draw off the fluid from the hybridization chamber. The cover wall displaced downwardly relative to the upper face of the frame facilitates the resilience of the entire cover. Consequently without the introduction of damaging forces in the support it can be more simply removed therefrom.

To attach pipette tips sealingly to the filling and ventilation holes, according to an embodiment the frame has a height of at least approximately 1.5 to 2 mm. For a resilient construction the cover wall has, according to an embodiment, a maximum wall thickness of approximately 1 to 2 mm.

According to an embodiment the frame is flat on the upper face and/or lower face and/or its outer face and/or inner face is inclined toward its upper face. As a result the sealed bond on the support and the flexibility of the cover is assisted.

On the upper face of the frame additional pressure can be exerted during hybridization on the frame, which assists the sealing of the adhesive joint. This is particularly advantageously possible with a planar upper face of the frame, plane parallel to the lower face. The pressure can for example be exerted via a plate on the frame.

According to an embodiment the frame is substantially rectangular and comprises filling and ventilation holes at diagonally opposing corners. Consequently steady filling, ventilating and optionally emptying of the hybridization chamber is assisted. According to an embodiment the frame bulges inwardly at the corners comprising filling and ventilation holes. These facilitate the filling and optionally the emptying process and the construction of a shoulder with a width which is advantageous for bonding with the support outside around the filling and ventilation holes.

According to an embodiment the shoulder is substantially strip-shaped for a flat and sealed bond with the support.

According to an embodiment the shoulder is guided in a curved shape around the filling and ventilation holes and rectilinear therebetween. According to an embodiment the filling and ventilation holes widen at least in one portion toward the upper face of the frame, whereby an advantageous contact and sealing face is provided for a pipette tip. To this end the filling and ventilation holes according to a further embodiment comprise a receiver adapted to the end of the pipette tip.

According to an embodiment a tab protruding parallel to the plane of the frame is present on an outer face of the frame. The tab is advantageous in particular for correctly aligning the cover relative to a microarray on a support and for removing the cover from the support. Thus according to a further embodiment the underside of the tab is flush with the lower face of the frame.

According to an embodiment the frame comprises an indentation on an outer face. The indentation facilitates the space-saving arrangement of a plurality of identically constructed covers next to one another with the indentations facing one another. Moreover the construction of the injection point in the region of the indentation is advantageous.

According to an embodiment the cover is transparent in the region of the cover wall and/or the frame. This favours visual observation of the filling and optionally the emptying processes. A transparent plastic material is used for this. According to a further embodiment at least the region of the cover wall is crystal clear. This is achieved for example by the use of injection moulds with highly polished surfaces.

According to an embodiment the cover is manufactured from a thermoplastic polyurethane and/or from a soft PVC. Furthermore materials can be used which have one or more of the following characteristics: resilience, suitability for bonding, transparency, extrudability, least possible binding of and/or release of DNA or RNA and/or fluorescent material.

The cover can in principle be manufactured from a plurality of resilient plastics. According to an embodiment it is manufactured integrally from one resilient plastics material.

The manufacture can be carried out in one or more injection steps. The cover can advantageously be manufactured integrally in a single injection step.

According to an embodiment a hybridization chamber comprises a support, immobilised biomaterial and at least one cover fastened to the support according to any of claims 1 to 18. Biomaterial refers for example to microarrays or tissue sections. According to an embodiment a bond is present between the support and the cover. The bond is for example formed by an adhesive application or double-sided adhesive tape.

The invention will be described below with reference to the accompanying drawings of an embodiment, in which:

FIGS. 1a to j are the cover in plan view (FIG. 1a), in a side view (FIG. 1b), in a rear view (FIG. 1c), in a section along the line A-A of FIG. 1a (FIG. 1d), in a section along the line A-A of FIG. 1a (FIG. 1e), in a section along the line C-C of FIG. 1a (FIG. 1f), in an enlarged detail D of FIG. 1e (FIG. 1g), in an angled perspective view from above (FIG. 1h), in a view from below (FIG. 1i) and in an angled perspective view from below (FIG. 1j);

FIGS. 2a and b are two chambers according to FIG. 1 on a support in an angled perspective view from above (FIG. 2a) and a reduced plan view (FIG. 2b);

FIGS. 3a and b are two chambers according to FIG. 1 on a support in a further angled perspective view from above (FIG. 3a) and in an angled perspective view from above from the other side (FIG. 3b).

According to FIG. 1a cover 1 has a peripheral frame 2 which is substantially rectangular. The frame 2 has inwardly facing bulges 3, 4 at diagonally opposing corners. At the corner with the bulge 4, the frame 2 has an indentation 5 on the outer face. Here two parallel portions of the same outer face are offset from one another, being connected to one another in the central region of this outer face by an angled portion.

The frame 2 has a flat upper face 6 and a flat lower face 7 parallel thereto. Moreover it comprises an outer face 8 and an inner face 9 surrounding it which are inclined toward the upper face 6.

In the corners with the bulges 3, 4 the frame 2 has filling and ventilation holes 10, 11 which extend from the upper face 6 to the lower face 7 of the frame. The filling and ventilation holes 10, 11 have a conical portion 10', 11' with a cup-shaped portion 10'', 11'' adjacent to the upper face 6. A tubular connecting portion 10''', 11''' is attached thereto. The tubular connecting portion 10''', 11''' is connected on the other face to a slightly conical end portion $10^{IV}$ (not shown), $11^{IV}$, which widens toward the lower face 7 into which it opens out.

The frame 2 has a downwardly protruding strip-shaped shoulder 12 on the lower face 7 which surrounds the entire frame 2. The shoulder 12 extends along the inner faces of the frame 2. Outside it is guided in a curved shape around the filling and ventilation holes 10, 11. Inside these curves 12' the lower face 7 extends within the shoulder 12 guided in a curved shape around the filling and ventilation holes 10, 11 as far as the inner face of the frame 2 in the region of the bulges 3, 4. The width of the shoulder 12 corresponds approximately to half the width (slightly more in the example) of the lower face 7.

The size of the conical portions 10', 11' and cup-shaped portions 10'', 11'' is such that the end of a standard pipette tip can be inserted, so that it is securely guided laterally and sealed.

Moreover the cover 1 has a cover wall 13, the upper face 14 thereof being downwardly offset relative to the upper face 6 of the frame 2, in the example measuring less than half the height of the frame 2 between its upper face 6 and its lower face 7.

The cover wall 13 has a lower face 15 which is axially aligned with the lower face 7 of the frame. In the regions of the bulges 3, 4 the lower face of the cover wall 15 and the lower face 7 of the frame 2 merge with one another.

Finally, the cover 1 has on the outer face of the frame 2 which lies opposite the outer face with the indentation 5, an outwardly protruding tab 16. The tab 16 is trapezoidal in plan view. Its lower face 17 is flush with the lower face 7 of the frame 2.

In the example the receiver for a pipette tip formed by the portions 10', 11', 10", 11" has a depth of approximately 2 mm. Accordingly, the height of the frame is approximately 4 mm and the wall thickness of the cover wall 13 approximately 1 to 2 mm.

The maximum external dimensions of the frame 2 on the faces with the tab 16 and the indentation 5 are approximately 35 mm and obliquely thereto approximately 25 mm.

In the example, the cover 1 is integrally injection moulded from a thermoplastic polyurethane (TPU) in a single step.

According to FIG. 2 two covers 1 of the aforementioned type are fixed to a support 18 made of glass. Here it refers to a rectangular sheet measuring 25×75 mm. Slides with these dimensions are widely available.

The two covers 1 are placed flush with the long outer faces of their frame 2 on the long outer faces of the slide 18. Moreover a cover 1 is placed flush with its tab 16 on a short outer face of the slide 18. The two covers 1 are placed with their indentations 5 against one another. By means of this arrangement the covers 1 are precisely positioned relative to the slide 18. Consequently microarrays previously placed on the slides 18 are located precisely under the region of the cover walls 13 of the two covers 1.

The covers 1 are for example bonded onto the slide 18 by means of double-sided adhesive tapes. These can already be prefixed to the covers 1. In this case it refers preferably to adhesive tapes which are provided with different adhesives toward the cover 1 and toward the slide 18 which ensure optimal bonding to the cover 1 and the slide 18, without affecting the carrying out of the hybridization. For example an acrylate-based adhesive is suited to the cover and a siliconised adhesive to the glass.

The shoulder 12 has a chamfer 19 (see FIGS. 1*i* and *j*) on the outside. The chamfer 19 facilitates the emergence of surplus adhesive, for example when adhering by means of an adhesive tape or by means of a specially applied adhesive.

The hybridization chambers formed by the covers 1 and the slide 18 are filled by attaching a pipette tip of a pipetting device to the filling holes 10 or 11 and by pressing in the fluid. In the process the air is forced out of the hybridization chamber through the ventilation holes 11 or 10, so that the entire cavity between the cover wall 13 and the support 18 is filled with fluid without bubbles. The possible evaporation of fluid during the hybridization lasting several hours is compensated for by the flexibility of the cover walls 13 which bulge slightly toward the inside. By vibrating the cover walls 13 when shaking, the mixture of fluid and thus the hybridization process is also intensified.

After completing the hybridization the fluid can be sucked out by means of a pipette tip through one of the filling and ventilation holes 10, 11. The fluid can however also remain in the cover. Finally, the covers 1 are peeled off the slide by pulling on the tabs 16, bending out in the direction of the applied force.

The invention claimed is:

1. Cover of a hybridization chamber with
   a peripheral frame (2) with filling and ventilation holes (10, 11) extending from the upper face (6) to the lower face (7) of the frame (2)
   a peripheral shoulder (12) outside the filling and ventilation holes on the lower face (7) of the frame,
   a cover wall (13) arranged inside the frame (2), flush with its lower face (7) and downwardly offset relative to its upper face (6) and
   which substantially consists of at least one resilient plastics material and which is integrally manufactured from a resilient plastics material 2. Cover according to claim 1, in which the frame has a height of at least approximately 1.5 to 2 mm and/or in which the cover wall (13) has a maximum wall thickness of approximately 1 to 2 mm.

3. Cover according to claim 1, in which the upper face (6) and/or the lower face (7) of the frame (2) is flat and/or the outer face (8) and/or the inner face (9) of the frame (2) is inclined toward its upper face (6).

4. Cover according to claim 1, the frame thereof being substantially rectangular and comprising filling and ventilation holes (10, 11) at diagonally opposing corners.

5. Cover according to claim 1, the frame (2) thereof comprising inwardly facing bulges (3, 4) at the corners comprising filling and ventilation holes (10, 11).

6. Cover according claim 1, the shoulder (12) thereof being substantially strip-shaped.

7. Cover according to claim 1, the shoulder (12) thereof being guided in a curved shape around the filling and ventilation holes (10, 11) and being rectilinear there between.

8. Cover according to claim 1, the filling and ventilation holes (10, 11) thereof then widening in a portion (10', 10", 11', 11") toward the upper face (6) of the frame (2).

9. Cover according to claim 1, the filling and ventilation holes (10, 11) thereof comprising a receiver (10', 10", 11', 11") adapted to the end of a pipette tip.

10. Cover according to claim 1, which comprises a tab (16) on an outer face of the frame (2) protruding parallel to the plane of the frame.

11. Cover according to claim 10, the tab (16) thereof being flush below with the lower face (7) of the frame (2).

12. Cover according to claim 1, the frame (2) thereof comprising an indentation (5) on an outer face.

13. Cover according to claim 1, which is transparent in the region of the cover wall (13) and/or the frame (2).

14. Cover according to claim 1, which at least in the region of the cover wall (13) is crystal clear.

15. Cover according to claim 1, which is manufactured from a thermoplastic polyurethane and/or from a soft PVC.

16. Cover according to claim 1, the underside of the shoulder (12) thereof being connected to a double-sided adhesive tape.

17. Cover according to claim 16 in which the double-sided adhesive tape comprises an acrylate adhesive toward the cover and a siliconised adhesive on the opposing face.

18. Hybridization chamber with a support (18), immobilized biomaterial on the support (18) and at least one cover (1) fastened onto the support (18) according to any of claims 1-15, 16 or 17.

19. Hybridization chamber according to claim 18, in which a bond is present between the support (18) and the cover (1).

* * * * *